United States Patent
Li et al.

(10) Patent No.: US 12,369,864 B2
(45) Date of Patent: Jul. 29, 2025

(54) REAL-TIME EVALUATION METHOD AND EVALUATION SYSTEM FOR GROUP EMOTION HOMOGENEITY

(71) Applicant: Zhejiang Lab, Zhejiang (CN)

(72) Inventors: Taihao Li, Zhejiang (CN); Guanxiong Pei, Zhejiang (CN); Yulong Liu, Zhejiang (CN)

(73) Assignee: Zhejiang Lab, Zhejiang (CN)

( * ) Notice: Subject to any disclaimer, the term of this patent is extended or adjusted under 35 U.S.C. 154(b) by 769 days.

(21) Appl. No.: 17/571,523

(22) Filed: Jan. 9, 2022

(65) Prior Publication Data
US 2022/0265218 A1    Aug. 25, 2022

(30) Foreign Application Priority Data
Feb. 22, 2021    (CN) .......................... 202110196796.2

(51) Int. Cl.
*A61B 5/00* (2006.01)
*A61B 5/31* (2021.01)
*A61B 5/372* (2021.01)
*A61B 5/378* (2021.01)

(52) U.S. Cl.
CPC ............. *A61B 5/7275* (2013.01); *A61B 5/31* (2021.01); *A61B 5/372* (2021.01); *A61B 5/378* (2021.01); *A61B 5/7203* (2013.01); *A61B 5/725* (2013.01)

(58) Field of Classification Search
CPC ........... A61B 5/31; A61B 5/372; A61B 5/378; A61B 5/7203; A61B 5/725; A61B 5/7275
See application file for complete search history.

(56) References Cited

U.S. PATENT DOCUMENTS
2022/0273226 A1* 9/2022 Song ....................... G06Q 30/02

OTHER PUBLICATIONS

Ding, Yue, et al. "Inter-brain EEG feature extraction and analysis for continuous implicit emotion tagging during video watching." IEEE Transactions on Affective Computing 12.1 (2018): 92-102. (Year: 2018).*

* cited by examiner

Primary Examiner — Devin B Henson
(74) Attorney, Agent, or Firm — JCIP GLOBAL INC.

(57) ABSTRACT

The present invention discloses a real-time evaluation method and evaluation system for group emotion homogeneity. The method comprises the steps as follows: enabling testees to be in the same emotion induction environment, and collecting the original electroencephalograph (EEG) signals of multiple persons at the same time through online multichannel EEG equipment; and based on the average instantaneous phase per second of the beta frequency band and the energy value per second of the alpha frequency band obtained after wavelet transformation, calculating the time synchronization degree and the valence consistency degree in real time, and finally obtaining a group emotion homogeneity index for the objective evaluation of group emotion homogeneity.

6 Claims, 2 Drawing Sheets

REAL-TIME EVALUATION METHOD AND EVALUATION SYSTEM FOR GROUP EMOTION HOMOGENEITY

CROSS-REFERENCE TO RELATED APPLICATION

This application claims the priority benefit of China application serial no. 202110196796.2, filed on Feb. 22, 2021. The entirety of the above-mentioned patent application is hereby incorporated by reference herein and made a part of this specification.

BACKGROUND

Technical Field

The present invention relates to the technical field of emotion calculation, in particular to a real-time evaluation method and evaluation system for group emotion homogeneity.

Description of Related Art

Emotion is known as the grammar of social living, and the recognition and understanding of emotion is one of the important functions of humanoid intelligent machines. Due to technical limitations and difficulties in implementation, previous studies have focused more on the emotional analysis and recognition at an individual level, while ignoring the emotion calculations at a group level. Group emotion refers to the common emotional experience of a crowd caused by the same external stimulus or mutual infection between individuals, including two aspects, namely time synchronization degree and valence consistency degree. At present, the measurement of group emotion homogeneity is still mainly carried out by traditional methods such as questionnaires, self-reports, behavior experiments, etc., and there is a lack of objective methods for calculating group emotion homogeneity in a proceduring manner.

SUMMARY

In order to solve the disadvantages in the prior art and achieve the purposes of real-time process and multi-person synchronous measurement with objective indexes for group emotion homogeneity, the present invention adopts the technical scheme as follows:

A real-time evaluation method for group emotion homogeneity comprises the steps as follows:

S1: Wearing multichannel electroencephalograph (EEG) measurement equipment for multiple testees at the same time;

S2: Enabling the testees to be in the same emotion induction environment, and synchronously collecting the original EEG signals of multiple testees;

S3: Performing real-time preprocessing and wavelet transformation for the original EEG signals from forehead and anterior temporal channels to obtain the average instantaneous phase per second of the beta frequency band, and calculating the energy value per second of the alpha frequency band in real time;

S4: Calculating the time synchronization degree in real time based on the average instantaneous phase, and calculating the valence consistency degree in real time based on the energy value;

S5: Calculating the group emotion homogeneity index in real time based on the time synchronization degree and the valence consistency degree;

S6: Conducting evaluation and grading for the group emotion homogeneity based on the curve of the group emotion homogeneity index changing along with time.

Further, the time synchronization degree in S4 is calculated by the formulae as follows:

$$T = \frac{2}{k(k-1)} \sum_{i=1}^{k} \sum_{j=1}^{k} \exp(S_{ij})$$

$$s_{ij} = \begin{cases} |x_i - x_j| & i < j \\ 0 & i \geq j \end{cases}$$

$$S = \begin{bmatrix} S_{11} & \cdots & S_{k1} \\ \vdots & \ddots & \vdots \\ S_{1k} & \cdots & S_{kk} \end{bmatrix}$$

$$S \in R^{k \times k}$$

where, T is the time synchronization degree, S is the real matrix for Row k and Line k, $S_{ij}$ is the value of phase difference, x represents the average instantaneous phase of the beta frequency band of a testee, i represents the $i^{th}$ testee in sequence, j represents the $j^{th}$ testee in sequence, and k is the total number of testees.

Further, the valence consistency degree in S4 is calculated by the formulae as follows:

$$V = \frac{1}{k} \max\{\|Y_{M_+}\|_1, \|Y_{M_-}\|_1\}$$

$$Y_{M_+} = \max\{Y_M, 0\}$$

$$Y_{M_-} = \min\{Y_M, 0\}$$

$$Y_M(i) = \begin{cases} 1 & M_i > 0 \\ 0 & M_i = 0 \\ -1 & M_i < 0 \end{cases}$$

$$M = (M_1, M_2, M_3, \ldots M_k)$$

$$M \in R^k$$

$$M_i = \log(PL_i) - \log(PR_i)$$

where, V is the valence consistency degree, $Y_M$ is a sign function, M is a k-dimensional vector, PL is the average value of energy of the alpha frequency band collected from the left forehead channel and the left anterior temporal channel of a testee, PR is the average value of energy of the alpha frequency band collected from the right forehead channel and the right anterior temporal channel of the testee, i represents the $i^{th}$ testee in sequence, and k is the total number of testees.

Further, the group emotion homogeneity index per second in S5 is calculated by the formula as follows:

$$E = V * T$$

where, E is the group emotion homogeneity index per second.

Further, the forehead and anterior temporal channels in S3 are selected by the method that: electrode points are configured according to the international 10-20 system and the distribution of related brain areas, and the electrode points of FP1, FPz, FP2, F7 and F8 are selected for calculating the emotion time synchronization degree, whereas the electrode points of FP1, FPz, FP2, Fz, F3, F4, F7 and F8 are selected for calculating the valence consistency degree.

Further, the standards for the evaluation and grading for homogeneity are as follows: the group emotion homogeneity index E≥0.6 is deemed as strong group emotion homogeneity, 0.4≤E<0.6 is deemed as convergent group emotion homogeneity, and E<0.4 is deemed as insufficient group emotion homogeneity.

Further, the multichannel EEG measurement equipment in S1 adopts 32-channel electrode caps and uses saline or gel electrodes, and the impedance of each electrode point is less than 5 kΩ.

A real-time evaluation system for group emotion homogeneity comprises an emotion induction device, an EEG measurement equipment group and a group emotion homogeneity calculation unit connected in order; wherein, the group emotion homogeneity calculation unit comprises a group EEG signal preprocessing module, a group emotion homogeneity calculation module and a data visualization module connected in order;

the emotion induction device is used as a stimulus to induce the emotion of testees;

the EEG measurement equipment group is used for synchronously collecting the EEG signals of multiple testees and transmitting the signals to the group EEG signal preprocessing module;

the group EEG signal preprocessing module is used for preprocessing the collected EEG signals by amplification, noise reduction and filtering;

the group emotion homogeneity calculation module is used for performing wavelet transformation for the EEG signals after preprocessing to obtain the average instantaneous phase per second of the beta frequency band, calculating the energy value per second of the alpha frequency band in real time, then calculating the time synchronization degree and the valence consistency degree in real time, and generating the group emotion homogeneity index;

the data visualization module is used for displaying the curve of the group emotion homogeneity index changing along with time.

Further, the preprocessing refers to the amplification, capturing analysis segments, noise reduction, artifacts removal and band-pass filtering for the collected EEG signals; the artifacts removal comprises removing the interference from electrooculogram, electromyogram, electrocardiogram and power frequency.

Further, the emotion induction device comprises an image displaying device and an image processing and storage device, and it is used for displaying emotion stimulating materials as a visual stimulus, as well as used for processing and storing the emotion stimulating materials.

The present invention has the advantages that:

1. The present invention forms a comprehensive calculation strategy on the two aspects of time synchronization degree and valence consistency degree and has the characteristic of real-time monitoring, and it can scientifically and comprehensively analyze the homogeneity of group emotion. At present, the researches on EEG recognition are mostly based on the amplitude feature and ignore the feature of phase synchronization among multiple brains. The feature of phase synchronization detects the interrelation between signal pairs by the instantaneous phase relation between signals, so that the synchronization of human nervous activities can be effectively recognized. Besides, the present invention creatively proposes a method for calculating group emotion valence depending on the energy of EEG frequency bands of specific brain areas, and the emotion recognition accuracy using SVM for two classification (positive, negative) reaches 95.4%.

2. The system of the present invention realizes multi-person synchronous real-time monitoring and dynamic analysis depending on the feature of high time resolution of EEG, it can research the the group emotion homogeneity in a proceduring and full-process manner, and effectively avoids the problems of after-event sampling, strong subjectivity, social desirability bias and the like of a traditional measurement means.

3. The system of the present invention with the functions of dynamic monitoring and visualization can help users intuitively obtain the data of group emotion homogeneity, so as to help to make a scientific decision. At the same time, owing to the characteristics of non-invasion, safety, high efficiency and lower cost, it can be commercially applied in the fields of film editing, evaluation on advertising effects, screening of emotion induction materials, evaluation on VR immersion effects, evaluation on the immersion experience of exhibition halls, prediction of audience rating, etc., and it has a wide market application prospect.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

The embodiment of the present invention will be described in detail below in combination with the drawings. It shall be understood that the embodiment described is used only for stating and explaining the present invention, rather than limiting the present invention.

Emotional experience is mainly triggered by environmental stimuli to cause the changes in brain functional activities, the response of the peripheral autonomic nervous system, and the changes in neurochemical substances in the body. An electroencephalograph (EEG) signal, as the overall reflection of the electrophysiological activities of brain nerve cells on the cerebral cortex or scalp surface, contains a large amount of physiological and psychological information related to emotions, and has the features of being direct and objective, difficult to disguise, easy to quantify, diversified characteristics, and it is the cognitive physiological index with the most significant effect in the field of emotion recognition. Through monitoring multi-person EEG signals at the same time, based on the correlation of intercerebral emotion related nervous activities, the group emotion homogeneity can be effectively monitored. A real-time evaluation method and evaluation system for group emotion homogeneity collect the EEG signal data of multiple persons using an online multichannel EEG equipment to perform the real-time dynamic analysis of group emotion, realizing the processing and displaying of agile data.

Figure 1:
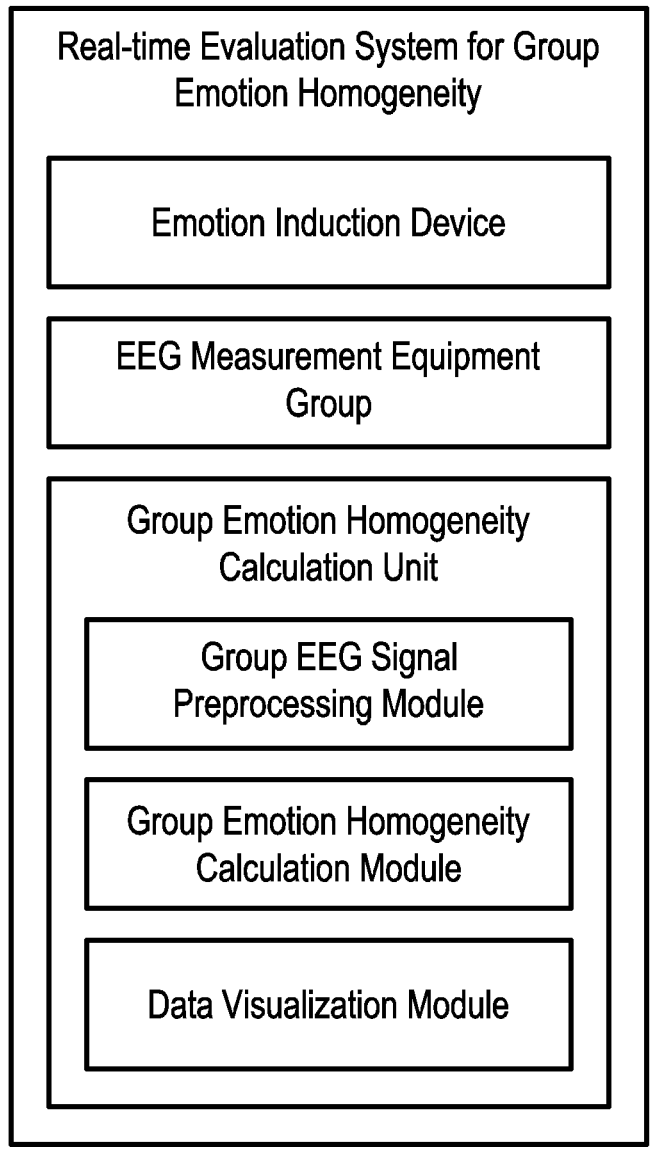
FIG. 1 is the structural chart of the system of the present invention.

As shown in FIG. 1, the real-time evaluation system for group emotion homogeneity comprises:

An emotion induction device comprising an image displaying device and an image processing and storage device, used for displaying emotion stimulating materials, and employing a screen as a visual stimulus according to the usual browsing habit. As an optional embodiment, a group of testees face a film screen for emotion induction by playing movie clips.

An EEG measurement equipment group, used for synchronously collecting the EEG signals of multiple testees and transmitting the signals to a group emotion homogeneity calculation unit. As an optional embodiment, the EMOTIV EPOC Flex Saline Sensor Kit EEG collection system (including a control box, a signal receiver, an EPOC Flex Cap and an EPOC Flex saline sensor) can be used, with a single ADC and a bandwidth of 0.16-43 Hz, containing 32-channel data, configuring 2 reference electrodes for ears, and realizing synchronous sequential sampling on multiple machines. The EMOTIV EPOC Flex series, with a high cost performance, suitable for the cost control of group measurement, was applied in clinical studies by relevant scholars. By comparing its data with those of expensive BP and Neuroscan equipments, it was found that there were quite small differences in the quality of the collected data. The configurations of the host for the system are: CPU: Intel Core i7-9700 or higher; GPU: NVIDIA GeForce GTX 2080 Ti or higher; memory: 64 GB RAM; 1 TB of free disk space.

A group emotion homogeneity calculation unit, comprising a group EEG signal preprocessing module, a group emotion homogeneity calculation module and a data visualization module. The group EEG signal preprocessing module is used for preprocessing the collected EEG signals by amplification, analysis segment capturing, noise reduction, artifacts removal (removing the interference from electrooculogram, electromyogram, electrocardiogram and power frequency) and band-pass filtering; the group emotion homogeneity calculation module is used for performing wavelet transformation for the EEG signals after preprocessing to obtain the average instantaneous phase per second of the beta frequency band, calculating the energy value per second of the alpha frequency band in real time, then calculating the time synchronization degree and the valence consistency degree in real time, and generating the group emotion homogeneity index; the data visualization module is used for displaying the profile of the group emotion homogeneity index over time, which helps users monitor the group emotion homogeneity and provides scientific evidence for decision-making.

Figure 2:
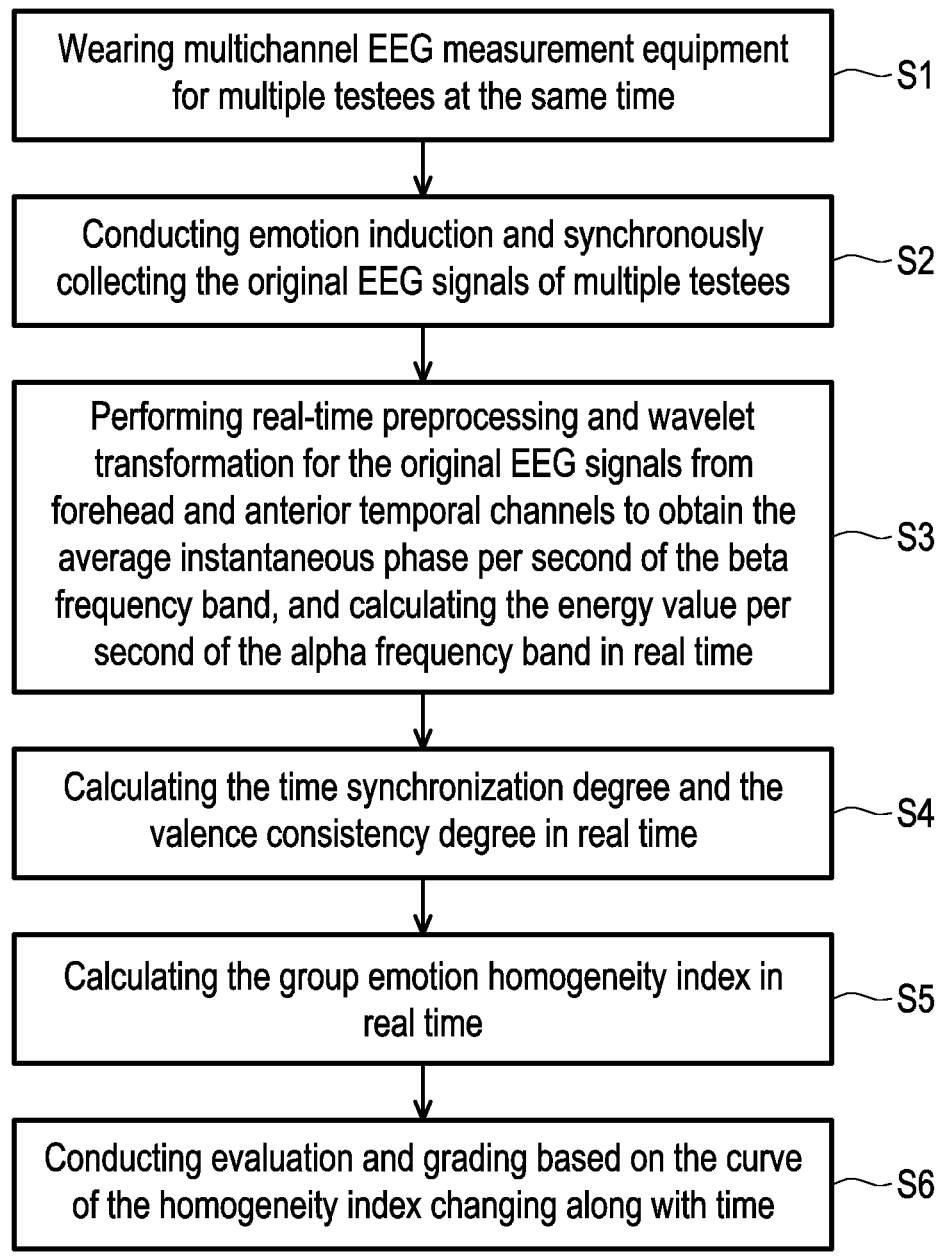
FIG. 2 is the flow chart of the system of the present invention.

As shown in FIG. 2, a real-time evaluation method for group emotion homogeneity, which is achieved based on the above real-time evaluation system, specifically comprises the steps as follows:

S1: Wearing multichannel EEG measurement equipment for multiple testees at the same time, adopting 32-channel electrode caps, and keeping the impedance of each electrode point at less than 5 kΩ by using saline or gel electrodes. An international uniform standard 10-20 system is used for the configuration for electrode positions.

S2: Placing the testees in the same emotion induction environment, and synchronously collecting the original EEG signals of multiple testees. The testees should minimize head movements or other body movements, avoid language communications among the testees, and reduce the interference of irrelevant visual or audio stimulus.

S3: Performing real-time preprocessing and wavelet transformation for the original EEG signals from forehead and anterior temporal channels to obtain the average instantaneous phase per second of the beta frequency band, and calculating the energy value per second of the alpha frequency band in real time. The forehead and anterior temporal channels are selected by the method that: electrode points are configured according to the international 10-20 system and the distribution of related brain areas, and the electrode points FP1, FPz, FP2, F7 and F8 are selected for calculating the emotion time synchronization degree, and the electrode points FP1, FPz, FP2, Fz, F3, F4, F7 and F8 are selected for calculating the valence consistency degree.

S4: Calculating the time synchronization degree in real time based on the average instantaneous phase obtained in S3, and calculating the valence consistency degree in real time based on the energy value obtained in S3;

The time synchronization degree T is calculated by the formulae as follows:

$$T = \frac{2}{k(k-1)} \sum_{i=1}^{k} \sum_{j=1}^{k} \exp(S_{ij})$$

$$S_{ij} = \begin{cases} |x_i - x_j| & i < j \\ 0 & i \geq j \end{cases}$$

$$S = \begin{bmatrix} S_{11} & \cdots & S_{k1} \\ \vdots & \ddots & \vdots \\ S_{1k} & \cdots & S_{kk} \end{bmatrix}$$

$$S \in R^{k \times k}$$

where, S is the real matrix for Row k and Line k, $S_{ij}$ is the value of phase difference, x represents the average instantaneous phase of the beta frequency band of a testee, i represented the $i^{th}$ testee in sequence, j represents the $j^{th}$ testee in sequence, and k is the total number of testees.

The valence consistency degree V is calculated by the formulae as follows:

$$V = \frac{1}{k} \max\{\|Y_{M_+}\|_1, \|Y_{M_-}\|_1\}$$

$$Y_{M_+} = \max\{Y_M, 0\}$$

$$Y_{M_-} = \min\{Y_M, 0\}$$

$$Y_M(i) = \begin{cases} 1 & M_i > 0 \\ 0 & M_i = 0 \\ -1 & M_i < 0 \end{cases}$$

$$M = (M_1, M_2, M_3, \ldots M_k)$$

$$M \in R^k$$

$$M_i = \log(PL_i) - \log(PR_i)$$

where, $Y_M$ is a sign function, M is a k-dimensional vector, PL is the average value of energy of the alpha frequency band collected from the left forehead channel and the left anterior temporal channel of a testee, PR is the average value of energy of the alpha frequency band collected from the right forehead channel and the right anterior temporal channel of the testee, i represents the $i^{th}$ testee in sequence, and k is the total number of testees.

S5: Calculating the group emotion homogeneity index in real time based on the time synchronization degree and the valence consistency degree in S4. The group emotion homogeneity index per second E is calculated by the formula as follows:

$$E = V*T$$

S6: Evaluating and grading the group emotion homogeneity based on the profile of the group emotion homogeneity index over time. The standards for evaluating and grading the homogeneity are as follows: the group emotion homogeneity index E≥0.6 is deemed as strong group emotion homogeneity, 0.4≤E<0.6 is deemed as convergent group emotion homogeneity, and E<0.4 is deemed as insufficient group emotion homogeneity.

According to the invention, multi-person synchronous real-time measurement and analysis are realized, the group emotion homogeneity can be dynamically monitored in a proceduring manner, the problems of after-event sampling, strong subjectivity, social desirability bias and the like of a traditional measurement means are effectively avoided, and the method has a wide market application prospect.

The embodiments above are only used for explaining, rather than limiting, the technical solutions of the present invention; although the present invention is explained in detail by reference to the above embodiments, those of ordinary skill in the art should understand that, they may modify the technical solutions recorded in the above embodiments, or equivalently replace a part or all of the technical features, whereas such modifications or replacements will not make the nature of the modified technical solutions deviate from the scope of the technical solution of the embodiment of the present invention.

What is claimed is:

1. A real-time evaluation method for group emotion homogeneity, wherein the method comprises steps as follows:
   S1: Wearing multichannel electroencephalograph (EEG) measurement equipment for multiple testees at the same time;
   S2: Enabling the testees to be in a same emotion induction environment, and synchronously collecting original EEG signals from a left forehead channel, a right forehead channel, a left anterior temporal channel and a right anterior temporal channel of each of the multiple testees;
   S3: Performing real-time preprocessing and wavelet transformation for the original EEG signals from forehead and anterior temporal channels to obtain an average instantaneous phase per second of a beta frequency band, and calculating an energy value per second of an alpha frequency band in real time;
   S4: Calculating a time synchronization degree in real time based on the average instantaneous phase, and calculating a valence consistency degree in real time based on the energy value;
   S5: Calculating a group emotion homogeneity index in real time based on the time synchronization degree and the valence consistency degree;
   wherein the time synchronization degree is calculated by formulae as follows:

$$T = \frac{2}{k(k-1)} \sum_{i=1}^{k} \sum_{j=1}^{k} \exp(S_{ij})$$

$$S_{ij} = \begin{cases} |x_i - x_j| & i < j \\ 0 & i \geq j \end{cases}$$

$$S = \begin{bmatrix} S_{11} & \cdots & S_{k1} \\ \vdots & \ddots & \vdots \\ S_{1k} & \cdots & S_{kk} \end{bmatrix}$$

$$S \in R^{k \times k}$$

where, T is the time synchronization degree, S is a real matrix for Row k and Line k, $S_{ij}$ is a value of phase difference, x represents an average instantaneous phase of the beta frequency band of the testee, i represents $i^{th}$ testee in sequence, j represents $j^{th}$ testee in sequence, and k is the total number of the testees;

S6: Conducting evaluation and grading for the group emotion homogeneity based on a curve of the group emotion homogeneity index changing along with time;

the valence consistency degree in S4 is calculated by formulae as follows:

$$V = \frac{1}{k} \max\{\|Y_{M_+}\|_1, \|Y_{M_-}\|_1\}$$

$$Y_{M_+} = \max\{Y_M, 0\}$$

$$Y_{M_-} = \min\{Y_M, 0\}$$

$$Y_M(i) = \begin{cases} 1 & M_i > 0 \\ 0 & M_i = 0 \\ -1 & M_i < 0 \end{cases}$$

where, V is the valence consistency degree, YM is a sign function, M is a k-dimensional vector, PL is an average value of energy of the alpha frequency band collected from the left forehead channel and the left anterior temporal channel of the testee, PR is an average value of energy of the alpha frequency band collected from the right forehead channel and the right anterior temporal channel of the testee, i represents the ith testee in sequence, and R is a set of real number;

wherein the group emotion homogeneity index per second is calculated by a formula as follows:

$$E = V*T$$

where, E is the group emotion homogeneity index per second;

wherein the group emotion homogeneity is strong in response to E≥0.6, the group emotion homogeneity is convergent in response to 0.4≤E<0.6, and the group emotion homogeneity is insufficient in response to E<0.4.

2. The real-time evaluation method for group emotion homogeneity according to claim 1, wherein the forehead and anterior temporal channels in S3 are selected by a method that: electrode points are configured according to an international 10-20 system and a distribution of related brain areas, and the electrode points of FP1, FPz, FP2, F7 and F8 are selected for calculating an emotion time synchronization degree, whereas the electrode points of FP1, FPz, FP2, Fz, F3, F4, F7 and F8 are selected for calculating the valence consistency degree.

3. The real-time evaluation method for group emotion homogeneity according to claim 1, wherein the multichannel EEG measurement equipment in S1 adopts 32-channel electrode caps and uses saline or gel electrodes, and an impedance of each electrode point is less than 5 kΩ.

4. A real-time evaluation system for group emotion homogeneity, comprising an emotion induction device, an EEG measurement equipment group and a group emotion homogeneity calculation unit connected in order; wherein the group emotion homogeneity calculation unit comprises a group EEG signal preprocessing module, a group emotion homogeneity calculation module and a data visualization module connected in order;

wherein the emotion induction device is configured to induce emotion of testees;

wherein the EEG measurement equipment group is configured to synchronously collect EEG signals from a left forehead channel, a right forehead channel, a left anterior temporal channel and a right anterior temporal channel of each of the multiple testees and transmit the EEG signals to the group EEG signal preprocessing module;

wherein the group EEG signal preprocessing module is configured to preprocess the collected EEG signals by amplification, noise reduction and filtering;

wherein the group emotion homogeneity calculation module is configured to perform wavelet transformation for the EEG signals after preprocessing to obtain an average instantaneous phase per second of a beta frequency band, calculate an energy value per second of an alpha frequency band in real time, then calculate a time synchronization degree and a valence consistency degree in real time based on the energy value, and generate a group emotion homogeneity index in real time based on the time synchronization degree and the valence consistency degree;

wherein the time synchronization degree is calculated by formulae as follows:

$$T = \frac{2}{k(k-1)} \sum_{i=1}^{k} \sum_{j=1}^{k} \exp(S_{ij})$$

$$S_{ij} = \begin{cases} |x_i - x_j| & i < j \\ 0 & i \geq j \end{cases}$$

$$S = \begin{bmatrix} S_{11} & \cdots & S_{k1} \\ \vdots & \ddots & \vdots \\ S_{1k} & \cdots & S_{kk} \end{bmatrix}$$

$$S \in R^{k \times k}$$

where, T is the time synchronization degree, S is a real matrix for Row k and Line k, $S_{ij}$ is a value of phase difference, x represents an average instantaneous phase of the beta frequency band of the testee, i represents $i^{th}$ testee in sequence, j represents $j^{th}$ testee in sequence, and k is the total number of the testees;

wherein the valence consistency degree is calculated by the formulae as follows:

$$V = \frac{1}{k} \max\{\|Y_{M_+}\|_1, \|Y_{M_-}\|_1\}$$

$$Y_{M_+} = \max\{Y_M, 0\}$$

$$Y_{M_-} = \min\{Y_M, 0\}$$

$$Y_M(i) = \begin{cases} 1 & M_i > 0 \\ 0 & M_i = 0 \\ -1 & M_i < 0 \end{cases}$$

$$M = (M_1, M_2, M_3, \ldots M_k)$$

$$M \in R^k$$

$$M_i = \log(PL_i) - \log(PR_i)$$

where, V is the valence consistency degree, YM is a sign function, M is a k-dimensional vector, PL is an average value of energy of the alpha frequency band collected from the left forehead channel and the left anterior temporal channel of the testee, PR is an average value of energy of the alpha frequency band collected from the right forehead channel and the right anterior temporal channel of the testee, i represents the $i^{th}$ testee in sequence, and R is a set of real number;

wherein the data visualization module is configured to display a curve of the group emotion homogeneity index changing along with time;

wherein the group emotion homogeneity index per second is calculated by a formula as follows:

$$E = V * T$$

where, E is the group emotion homogeneity index per second;

wherein the group emotion homogeneity is strong in response to E≥0.6, the group emotion homogeneity is convergent in response to 0.4≤E<0.6, and the group emotion homogeneity is insufficient in response to E<0.4.

5. The real-time evaluation system for group emotion homogeneity according to claim 4, wherein the preprocessing refers to the amplification, capturing analysis segments, noise reduction, artifacts removal and band-pass filtering for the collected EEG signals; the artifacts removal comprises removing an interference from electrooculogram, electromyogram, electrocardiogram and power frequency.

6. The real-time evaluation system for group emotion homogeneity according to claim 4, wherein the emotion induction device comprises an image displaying device and an image processing and storage device, and the emotion induction device is configured to display emotion stimulating materials as a visual stimulus, as well as used for processing and storing the emotion stimulating materials.

* * * * *